United States Patent [19]
Dertinger et al.

[11] Patent Number: 6,100,038
[45] Date of Patent: Aug. 8, 2000

[54] METHOD FOR THE ENUMERATION OF MICRONUCLEATED ERYTHROCYTE POPULATIONS WITH A SINGLE LASER FLOW CYTOMETER

[75] Inventors: Stephen D. Dertinger, Webster; Dorothea K. Torous; Kenneth R. Tometsko, both of Rochester, all of N.Y.

[73] Assignee: Litron Laboratories Limited, Rochester, N.Y.

[21] Appl. No.: 09/228,329

[22] Filed: Jan. 11, 1999

Related U.S. Application Data

[63] Continuation-in-part of application No. 08/706,680, Sep. 6, 1996, Pat. No. 5,858,667.

[51] Int. Cl.[7] .............................. C12Q 1/68; G01N 33/53; G01N 33/566; G01N 33/563; C07K 16/00
[52] U.S. Cl. .................... 435/6; 435/6; 435/7.1; 435/7.2; 435/7.95; 435/334; 435/355; 435/810; 435/968; 436/501; 436/513; 436/521; 436/536; 436/94; 436/800; 530/388.7; 530/387.1; 935/76; 935/77
[58] Field of Search ................... 435/6, 7.1, 7.2, 435/7.95, 334, 355, 810, 968; 436/501, 513, 521, 536, 94, 800; 530/387.1, 388.7; 935/76, 77

[56] References Cited

PUBLICATIONS

Zheng et al., Flow Sorting of Fetal Erythroblasts using intracytoplasmic anti–fetal haemoblobin, Prenatal Diagnosis, 15(10) 897–905 (1995).

Dertinger et al, "Simple and reliable enumeration of micronucleated reticulocytes with a single–laser flow cytomer," Mutation Research, vol. 371, pp. 283–292 (1996).

Begg et al, "Cell Kinetic Analysis of Mixed Populations Using Three–Color Fluorescence Flow Cytometry," Cytometry, vol. 12, pp. 445–454 (1991).

Tometsko et al., "Analysis of micronucleated cells by flow cytometry," Mutation Research, vol. 334, pp. 9–18 (1995).

Graham et al., "Simultaneous Measurement of Progesterone Receptors and DNA Indices by Flow Cytometry: Characterization of an Assay in Breast Cancer Cell Lines," Cancer Research, vol. 49, pp. 3934–3942 (1989).

Tonevitsky et al., "Elimination of Murine Erythroleukemic Stem Cells with a Novel Anti–Erythroid Antibody Conjugated to Ricin A–Chain: A Model for Studies of Bone–Marrow Transplantation Therapy," Int. J. Cancer, vol. 37, pp. 263–273 (1986).

Ievleva et al., "Specific Antigen of Murine Erythroblasts," Int. J. Cancer, vol. 17, pp. 798–805 (1976).

(List continued on next page.)

*Primary Examiner*—James C. Housel
*Assistant Examiner*—Gailene R. Gabel
*Attorney, Agent, or Firm*—Hodgson, Russ, Andrews, Woods & Goodyear, LLP

[57] ABSTRACT

A single laser flow cytometric method for the enumeration of micronuclei in erythrocyte populations, wherein a sample of peripheral blood or bone marrow is obtained and the cell populations in the sample are fixed. Reticulocytes in the fixed samples are treated simultaneously with RNAse and with a fluorescent labeled antibody having binding specificity for a surface marker for erythroblasts/reticulocytes. The erythrocyte populations are then stained with a nucleic acid stain which stains DNA representing micronuclei, if present. The stained and/or labeled erythrocyte populations are then exposed to a laser beam of appropriate excitation wavelength for both the nucleic acid staining dye and the fluorescent label to produce fluorescent emission. The fluorescent emission and light scatter produced by the erythrocyte populations are detected by the flow cytometer from which is calculated the number of specific erythrocyte populations in said sample.

27 Claims, 8 Drawing Sheets

OTHER PUBLICATIONS

Andrews et al., "Myeloid–Associated Differentiation Antigens on Stem Cells and Their Progeny Identified by Monoclonal Antibodies," Blood, vol. 62, pp. 124–132 (1983).

Edelman et al., "A Monoclonal Antibody Against an Erythrocyte Ontogenic Antigen Identifies Fetal and Adult Erythroid Progenitors," Blood, vol. 67 pp. 56–663 (1986).

Sancho et al., "Tranferrin Binding Capacity as a Marker of Differentiation and Maturation of Rat Erythroid Cells Fractionated by Counter Current Distribution in Aqueous Polymer Two–Phase Systems," Bioscience Reports, vol. 14, No. 3, 1994.

Ievleva et al., Eksp Onkol. 8:27–28, 1986, English Abstract Only.

6,100,038

METHOD FOR THE ENUMERATION OF MICRONUCLEATED ERYTHROCYTE POPULATIONS WITH A SINGLE LASER FLOW CYTOMETER

This application is a continuation-in-part of, U.S. patent application Ser. No. 08/706,680, filed on Sep. 6, 1996, now U.S. Pat. No. 5,858,667.

FIELD OF THE INVENTION

This invention is directed to medical applications, and the field of toxicology, in which a need exists for a rapid, sensitive and economical method for evaluating micronucleated erythrocytes. Specifically, the present invention relates to a process for analyzing the frequency of micronuclei in erythrocyte populations from peripheral blood or bone marrow by a rapid and sensitive single-laser flow cytometric method.

BACKGROUND OF THE INVENTION

The in vivo micronucleus test, as performed in laboratory rodents, has gained widespread use as a short-term system to screen chemicals for clastogenic (chromosome-breaking) or aneugenic activity. The test is based on the observation that mitotic cells with either chromatid breaks or dysfunctional spindle apparatus exhibit disturbances in the anaphase distribution of their chromatin. After telophase, this displaced chromatin can be excluded from the nuclei of the daughter cell and is found in the cytoplasm as a micronucleus. Traditionally, micronuclei were scored in bone marrow preparations. An important advance came with the observation that micronucleated erythrocytes are not cleared from the blood of mice, thus allowing the analysis to be carried out more readily with peripheral blood samples. Erythrocytes are particularly well suited for evaluating micronuclei events since the nucleus of the erythroblast is expelled a few hours after the last mitosis yielding DNA deficient cells. Consequently, micronuclei are apparent in this cell population which is otherwise devoid of DNA. Treatment with clastogens and/or spindle poisons which cause genotoxic damage to stem cells results in the formation of easily detectable micronuclei in these young anucleated reticulocytes. These young anucleated cells are still rich in RNA and certain surface markers (e.g., CD71) and with appropriate staining can be distinguished from the mature normochromatic erythrocytes. From the bone marrow, these reticulocytes enter the bloodstream where they complete their evolution to RNA deficient normochromatic erythrocytes. By scoring micronuclei exclusively in the short-lived reticulocyte population, variation to micronuclei frequency can be attributed to a recent cell cycle, making the system amenable to acute exposure protocols.

Historically, micronucleus analyses have been conducted in rat bone marrow as opposed to rat peripheral blood because the rat spleen is able to capture and remove circulating micronucleated erythrocytes from peripheral circulation. However, recent reports have demonstrated the suitability of rat peripheral blood for micronucleus assessment when the analysis is restricted to the youngest of the immature RET population (i.e. Type I and II reticulocytes). The result is a sensitive index of genotoxicity (Wakata et al., 1998, *Environmental and Molecular Mutagenesis,* 21:136–143).

Analogous to microscopists restricting micronucleus scoring to Type I and Type II RETs based on RNA content, flow cytometric analysis can be limited to the youngest fraction of RETs based on the level of certain cell surface markers (e.g. CD71 or transferrin receptor expression). Fluorescent antibodies directed against the transferrin receptor are used to label the RET population. This immunofluorescent labeling procedure has been found to closely parallel the RET enumeration methods based on RNA content (Dertinger et al., 1996, *Mutation Research,* 371:283–292). Due to the direct relationship between RET maturity and CD-71 content, it is possible to characterize RETs according to age with this technique.

This modification to the mouse assay, which results in sensitive indications of genotoxicity in the rat peripheral blood compartment, has important implications for human biomonitoring. The spleen of the rat behaves very similarly to that of humans with regards to the effective scavenging of circulating micronucleated erythrocytes. Therefore, as with the rat, it is important to limit human peripheral blood micronucleus analyses to the youngest RETs (unless the individual is splenectomized).

An assay for micronucleated erythrocytes has applications as a system to evaluate nutrition or disease processes in humans. For example, in folate deficient humans, the frequency of micronucleated polychromatic erythrocytes appears to be associated with diet (Tucker et al., 1993, *Mutat. Res.* 301:19–26). Similarly, in splenectomized individuals, an increase in the frequency of micronucleated polychromatic erythrocytes has been associated with dietary factors, such as coffee and tea consumption (Smith et al., 1990, *Cancer Res.* 50:5049–5054; MacGregor et al., 1990, *Proc. Natl. Acad. Sci.*). Additionally, it is noted that various nucleoside analogues are being extensively used in the treatment of HIV-infected individuals. These analogues, used to inhibit replication of the virus, also significantly increase the frequency of micronucleated polychromatic erythrocytes in treated individuals (Phillips et al., 1991, *Environ. Mol. Mutagen.* 18:168–183. Thus, the frequency of micronuclei events in such individuals may be an additional indicator useful in monitoring nucleoside analog therapy.

The spontaneous background level of micronuclei in blood cells is usually quite low (approximately 2 micronuclei/1000 cells). The rarity of the micronuclei events coupled with the low throughput capacity of microscopic scoring procedures makes the conventional assay labor intensive and time consuming. The scoring operations are subject to human errors arising from the level of experience of each technician. Furthermore, assay sensitivity may be low due to the relatively small number of cells that are processed using the traditional microscopy-based scoring procedure. Manually scoring the slides for micronuclei takes weeks and is labor intensive. Practitioners of the art realize the need for automated methods to objectively and accurately score larger numbers of micronucleated cells thereby improving assay sensitivity and reliability.

At the present time in this art, the most rapid and accurate way to enumerate micronucleated erythrocytes in the total peripheral blood erythrocyte pool is by a flow cytometric method. One such method is disclosed in U.S. Pat. No. 5,229,265 (to the same Assignee hereof, the disclosure of which is herein incorporated by reference). In a flow cytometric method, cells pass in single file through a laser beam where a cell's fluorescence and light scatter properties are determined. In contrast to manual methods where only 1000–2000 cells per sample are scored, modern flow cytometers are capable of processing cells at rates in excess of 8,000 cells/second. By evaluating more cells, greater scoring accuracy is achieved. A considerable challenge has been to develop reliable automated methods for quantitating micronuclei events in peripheral blood and bone marrow reticulocytes. The advantage of restricting the analysis to these newly formed cells is that this population can highlight genotoxic or cytogenetic action resulting from acute exposures.

Classically, reticulocytes are divided into five populations which are defined by the staining pattern observed in the presence of RNA-precipitating dyes. Stains such as thiazole orange (Lee et al., 1986, *Cytometry* 7:508–516) and acridine orange (Seligman et al., 1983, *Am. J. Hematology* 14:57–66) are widely employed. However, in regards to a flow cytometry-based micronucleus assay, these and other RNA dyes are problematic. Since RNA dyes actually bind to DNA as well, overlapping signals tend to limit the resolution of micronucleated reticulocytes from micronucleated normochromatic erythrocytes. A flow cytometric method utilizing a dual dye combination consisting of thiazole orange and Hoechst 33342 has been described (Grawe et al., 1992, *Cytometry* 13:750–758). Thiazole orange stains the RNA component of the reticulocyte population, and Hoechst dye is used to label micronuclei. The dissimilar wavelengths necessary for the excitation of DNA and RNA dyes necessitates the use of a dual-laser flow cytometer.

Accordingly, there is a need in this art for a rapid, simple and accurate technique to determine the changes in the micronucleated cell populations in the blood and bone marrow cells caused by the action of genotoxic agents. Such a technique would desirably use reticulocyte and micronuclei-specific labels that are excited by a similar wavelength but exhibit significantly different emission spectra, thus enabling the use of a single-laser flow cytometer in a flow cytometric-based micronucleus assay.

SUMMARY OF THE INVENTION

An object of this invention is to provide a single-laser flow cytometric method for simultaneously and separately quantitating micronuclei events in the mature normochromatic erythrocyte population and the immature reticulocyte population. In the method of the present invention, fluorescent-labeled antibodies directed against a surface marker for erythroblasts (representing a certain differentiation stage of erythroid cells) are used to label the reticulocyte population, and a nucleic acid staining dye is utilized to resolve the micronuclei events. An important advantage of this procedure is that these reticulocyte and micronuclei-specific labels are excited by a similar wavelength, but exhibit significantly different emission spectra, thus enabling the use of a single-laser flow cytometer in the flow cytometry-based micronucleus assay according to the present invention.

The method according to the present invention effectively analyzes the erythrocyte populations for the presence of micronuclei and can be used to evaluate the genotoxic activity associated with experimentally defined conditions. The capability of providing micronuclei frequencies in both the normochromatic erythrocyte population and the reticulocyte population makes the method compatible with both subchronic and acute treatment protocols; i.e., given the capability of discriminating between young and old erythrocytes, the method lends itself to both acute and subchronic dosing regimens.

Another object of the present invention is to provide a flow cytometry-based micronucleus assay that supplies repeatable and reliable data with technical ease and modest equipment requirements. The method described herein allows for the flow cytometric analysis, using a single-laser flow cytometer, of the micronucleated normochromatic erythrocyte and micronucleated reticulocyte cell populations in peripheral blood samples or in bone marrow preparations. The invention provides details concerning sample preparation and instrument configuration. The process is able to analyze thousands of erythrocytes in each blood or bone marrow sample in minutes, thereby enhancing the accuracy of the measurements.

BRIEF DESCRIPTION OF THE DRAWINGS

FIG. 1*a* is in logarithmic scale and FIG. 1*b* is in linear scale.

DESCRIPTION OF THE PREFERRED EMBODIMENTS

Figure 1A:
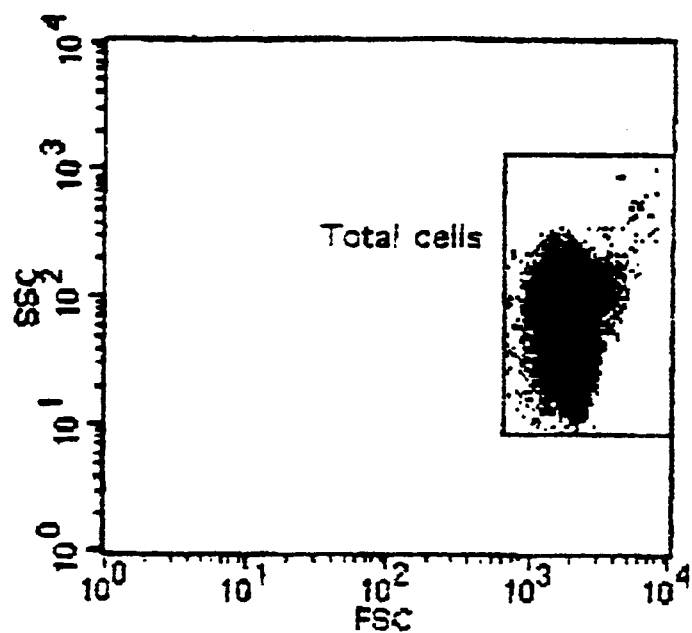
FIG. 1*a* and 1*b* is a bivariate graphs of FCS versus SSC for Plamodium berghei infected blood.

Definitions:

By the term "erythrocyte populations" is meant, for the purposes of the specification and claims, populations of mature normochromatic erythrocytes, immature erythrocytes such as erythroblasts and/or reticulocytes, micronucleated normo-chromatic erythrocytes, micronucleated reticulocytes, and a combination thereof from peripheral blood or bone marrow origins. By the term "a surface marker for erythroblasts/reticulocytes" is meant, for the purposes of the specification and claims, at least one species of a surface molecule present on reticulocytes but absent on mature erythrocytes, thereby enabling reticulocytes to be distinguished from mature erythrocytes by the presence of this marker. Such markers are known in the art to include, but are not limited to, CD71 (a transferrin receptor; Sancho et al., 1994, *Biosci. Rep.* 14:119–130); a 69 kDa molecule recognized by monoclonal antibody MAE15 (Tonevitsky et al., 1986, *Int. J. Cancer* 37:263–273); a molecule recognized by monoclonal antibody FA6-152 (Edelman et al., 1986, *Blood* 67:56–63); a molecule(s) recognized by monoclonal antibodies HAE3 and HAE9 (Ievleva et al., 1986, *Eksp Onkol* 8:27–28); a molecule referred to as Ag-Eb, antigen of erythroblasts (Ievleva et a., 1976, *Int. J. Cancer* 17:798–805); and an antigenic determinant recognized by monoclonal antibody 5F1 (Andrews et al., 1983, *Blood* 62:124–132). One or more of these markers are present on mammalian species other than mice. For example, CD71 is present on human and rat reticulocytes but absent on mature erythrocytes. As illustrated by the above-listed references, it is a standard procedure known to those skilled in the art to make a monoclonal antibody specific for such a marker (see, e.g., Edelman et al., wherein mice were immunized with fetal erythrocytes). Such monoclonal antibodies may be useful in the single-laser flow cytometric method-based micronucleus assay according to the present invention.

By the term "fluorescent label" is meant, for the purposes of the specification and claims, at least one species of a fluorescent molecule which is conjugated or otherwise attached to a monoclonal antibody with binding specificity for a surface marker for erythroblasts/reticulocytes. While other fluorescent labels known in the art may be useful in the method according to the present invention, fluorescent labels having an excitation wavelength of in a range of about 485 to 491 nanometers (nm) and an emission wavelength for detection in a range of about 515 to 525 nm are desirable. Such fluorescent labels include, but are not limited to fluorescein isothiocyanate (FITC), carboxy-fluorescein succinimidyl ester, 5-iodoacetamidofluorescein, and fluorescein maleimide.

By the terms "nucleic acid staining dye" is meant, for the purposes of the specification and claims, a dye that has a excitation wavelength in the range of that of the fluorescent label used, and includes, but is not limited to propidium iodide, ethidium bromide, mithramycin, acridine orange, pyronine Y, and benzathiazolium-4-quinolinium dimer TOTO-1. By the terms "individual" or "mammal" is meant, for the purposes of the specification and claims, a mammal species including, but not limited to mouse, rat, and human.

The process of this invention is broad in scope and, consequently, the preferred embodiments cover many disciplines which lead to reliable and reproducible flow cytometry-based micronucleus analyses. The description of the preferred embodiment pertains to procedures necessary to analyze erythrocyte populations for the presence of micronuclei. The description will therefore directly parallel the operation that would be carried out in a typical micronucleus assay.

The method of the present invention can also be used in mammals (e.g., rat, man) in which the spleen is known to capture and remove circulating micronucleated erythrocytes from peripheral blood. By utilizing the cell surface markers targeted in this invention, analysis is restricted to the youngest fraction of RETs which have not yet been captured by the spleen.

EXAMPLE 1

Fixing Blood Cells For Analysis By Flow Cytometry

A suitable and reproducible fixing procedure is necessary to provide cells from erythrocyte populations that are compatible with subsequent staining and analysis by flow cytometry. For the present invention, the fixing procedure must provide cells with the following characteristics: (1) in suspension and free of aggregates; (2) permeability to nucleic acid staining dyes and RNAse; (3) bearing a CD71 antigen or other surface marker for erythroblasts/reticulocytes recognition by a respective antibody; and (4) low autofluorescence. While there may be several fixing procedures known to those skilled in the art that are suitable for use with the method according to the present invention, a description of a preferred fixing procedure follows.

Peripheral Blood

Peripheral blood samples are obtained from the individual for analysis. For example, a blood sample can be obtained from the tail vein of male and/or female rodent after a brief warming period under a heat lamp. Blood samples (50–200 µl) are collected into tubes containing 100–500 µl anticoagulant solution (e.g., 500 USP units heparin/ml buffered saline). Blood samples are maintained at room temperature until they are fixed (within about 2–6 hours). Fixation is achieved by forcefully delivering a 100–250 µl aliquot of each blood suspension from a pipettor into separate polypropylene centrifuge tubes containing about 1–3 ml ultracold (between about −40° C. to about −90° C., preferably −70° C.) alcohol. The alcohol may be a primary alcohol, including, but not limited to, ethanol or methanol, or a secondary alcohol, including, but not limited to isopropyl alcohol. In a preferred embodiment, the alcohol is methanol. The tubes are struck sharply several times to break up any aggregates, and stored at between about −40° C. to about −90° C., preferably −70° C. for at least 24 hours. Prior to analysis, the cells are diluted out of the methanol with about 8 ml to 12 ml ice cold 0.9% NaCl solution which is supplemented with 5.3 mM sodium bicarbonate (hereinafter referred to as "bicarbonate buffer"). The cells are centrifuged at 500 to 1000× g for 5 minutes at room temperature, the supernatants are decanted, and the cell pellets are stored at 4° C. until analysis. This ultracold methanol procedure is considered optimal. It has been found to be both technically simple and highly reproducible. Importantly, the method does not generate undesirable auto-fluorescence as is the case with glutaraldehyde, a fixative which limits the resolution of fluorescein isothiocyanate (FITC)-labeled reticulocytes. A critical parameter of the alcohol fixation procedure of the present invention is temperature. For example, cells are added to a fixative which is in the temperature range of about −40° C. to about −90° C. A more preferable range is −70° C. to −90° C. methanol. At this stage, the erythrocytes are stable at −40° C. to −90° C. indefinitely. After cells are washed with bicarbonate buffer, it is important to maintain them at 4° C. If cells are kept at room temperature for long periods of time, unacceptable degradation of the cell's light scatter and fluorescent staining characteristics results. Washed cells maintained at 4° C. are stable for at least one week and are then ready for staining and micronucleus analysis.

Bone Marrow cells

As with the peripheral blood, a crucial criterion for reliable micronucleus scoring in bone marrow erythrocyte populations is the utilization of an optimized fixing protocol. A further consideration in the bone marrow procedure is that there is a higher potential for unwanted debris. A preferred harvesting and fixing procedure follows.

Procedures are known to those skilled in the art for obtaining a bone marrow aspirate from an individual. In rodents, the femur (i.e., thigh bone) is removed and stored in a suitable tissue culture medium (e.g., Dulbecco's Modified Eagle Medium, DMEM, and QBSF-58) at 4° C. to 25° C. The femur is cleaned to remove attached tissue, and is then washed with the culture medium. One end is cut, and the marrow is gently flushed out with about 300 $\mu$l to 1000 $\mu$l medium via a syringe with an attached small gauge (26.5) needle. The cell suspension from the bone marrow sample is then transferred to a tube where debris is allowed to settle out for 10 minutes. The cell suspension may then be passed through a 35–70 micron mesh filter to help eliminate any remaining debris. As with peripheral blood samples, fixation is achieved by forcefully delivering a 100–250 $\mu$l aliquot of each bone marrow cell suspension from a pipettor into separate polypropylene centrifuge tubes containing ultracold (between about −40° C. to about −90° C., preferably −70° C.) methanol. The tubes are struck sharply several times to break up any aggregates, and stored at between about −40° C. to about −90° C., preferably −70° C. for at least 24 hours. Prior to analysis, the cells are diluted out of the methanol with 8 ml to 12 ml ice cold bicarbonate buffer. The cells are centrifuged at 500 to 1000× g for 5 minutes at room temperature, the supernatants are decanted, and the cell pellets are stored at 4° C. until analysis. Washed cells maintained at 4° C. are stable for at least one week, and are ready for staining and micronucleus analysis utilizing procedures suitable for the method according to the present invention.

EXAMPLE 2

Flow cytometer setup

Optimum flow cytometer settings are extremely important in this process. The fluorescent signals of the stained micronucleated normochromatic erythrocyte and micronucleated reticulocyte populations should be clearly resolved from those of the normochromatic erythrocyte and reticulocyte cell populations. In accordance with the method of the present invention, the analyses described herein were carried out with a single laser flow cytometer (Fac Star$^{Plus\ TM}$, Becton Dickinson). The 5 W argon ion laser was tuned to provide 488 nm excitation. Cells were passed through the laser at an average rate of 2,500–8,000 erythrocytes/second. One embodiment of the invention is to use a 20 $\mu$ elliptical beam that is focused at the sample stream. The results and analyses described herein were obtained with said beam. As known to those skilled in the art, different beam shapes are also acceptable.

Figure 4:
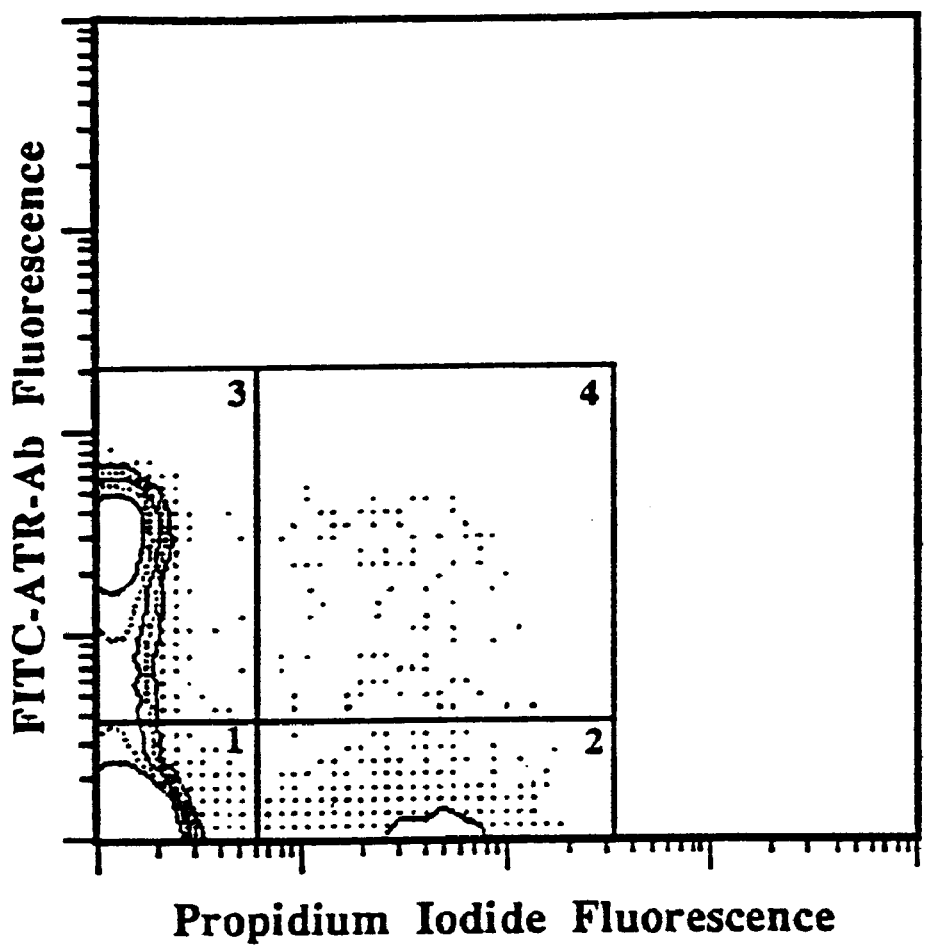
FIG. 4. is a bivariate graph illustrating the resolution of the mouse erythrocyte populations. Window no. 1 corresponds to cells which are low in green and red fluorescence, i.e., normochromatic erythrocytes. Window no. 2 corresponds to cells high in red fluorescence, i.e., micronucleated normo-chromatic erythrocytes. Window no. 3 corresponds to cells high in green fluorescence, i.e., reticulocytes. Window no. 4 corresponds to cells high in both red and green fluorescence, i.e., micronucleated reticulocytes.

The flow cytometer is equipped with four photomultiplier tubes (PMTs) which are used to sense forward light scatter, side light scatter, red fluorescence signals, and green fluorescence signals. Proper filters must be placed before the green and red photomultiplier tubes. In accordance with the methods of the present invention, adequate fluorescent signals can be obtained if a 520 nm long pass filter and a 555 nm short pass filter is placed before the green PMT. In accordance with the methods of the present invention, a 580 nm long pass filter in front of the red PMT is desirable. This is a preferred configuration that allows optimal fluorescence detection. However, as known to those skilled in the art, other filter sets may be acceptable. The signals received by the PMTs and the light scatter photodiode are processed by an in-line computer and cell populations of interest are quantitated (see, e.g., FIG. 4) using software conventional to the art. The data may be acquired and processed as either logarithmic or linear signals. In one configuration of the invention, log data was acquired for the forward light scatter, side scatter, as well as red and green fluorescence peak height signals.

Figure 1B:
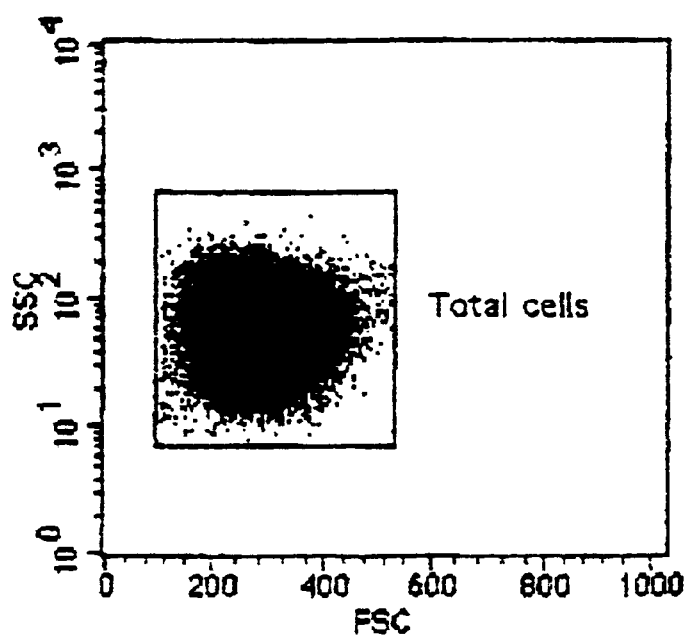
Figure 2:
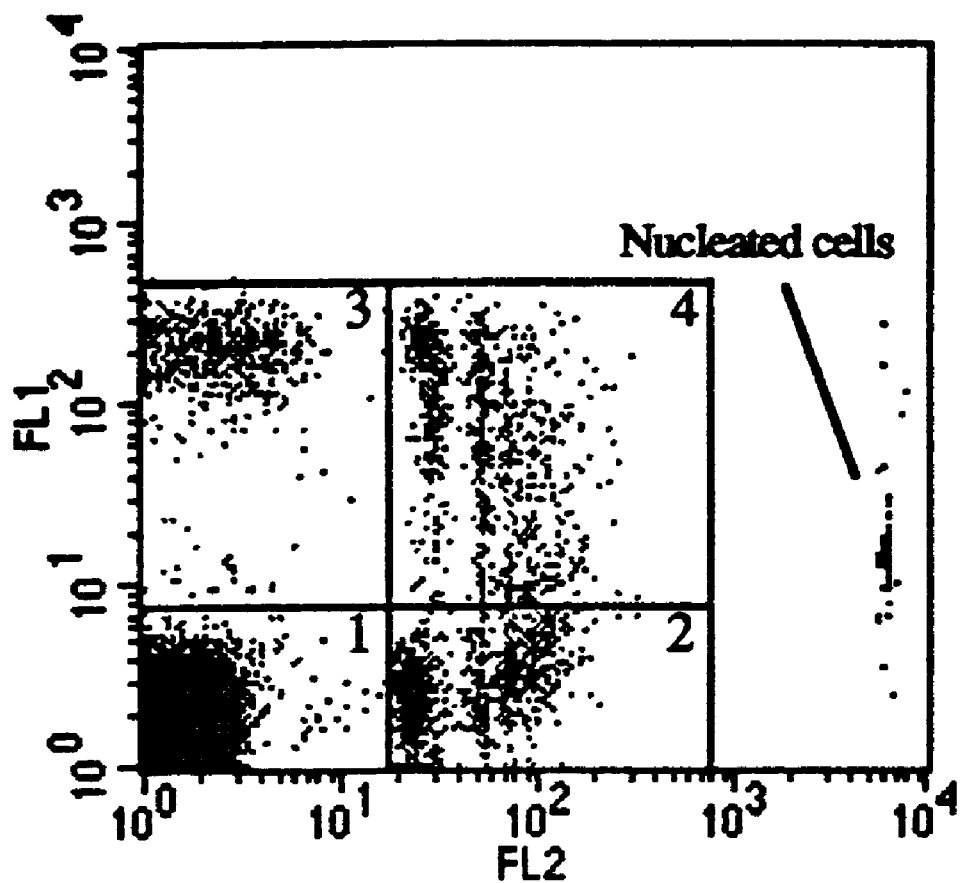
FIG. 2 is a bivariate plot of green fluorescence (FL1) versus red fluorescence (FL2) for Plasmodium berghei infected blood showing the resolution of the various cell populations. Window no. 1 corresponds to cells which are low in green and red fluorescence, i.e. normochromatic erythrocytes. Window no. 2 corresponds to cells high in red fluorescence, i.e. parasitized normochromatic erythrocytes. Window no. 3 corresponds to cells high in green fluorescence, i.e. reticulocytes. Window no. 4 corresponds to cells high in both red and green fluorescence, i.e. parasitized reticulocytes.

The analysis of the stained cells relies further upon properly setting and adjusting the flow cytometer for micronucleus analysis. Malarial parasite (Plasmodim berghei) infected blood provides a good control since the DNA content of the parasite is regulated by genetics. Red blood cells that contain single or multiple parasites give relatively sharp fluorescent peaks can be used to align the flow cytometry for micronucleus analysis. The parasitized blood is stained in parallel with the test samples, so that adjustments to flow cytometer settings can be made inorder to compensate for subtle changes in cell staining. Even if different laser powers are channels on histogram or bivariate graphs can be achieved by those skilled in the art, by adjusting the PMT voltages or fluorescence compensation. Fixed and stained malaria blood can this be used to compensate for subtle variations in the conditions and settings of the flow cytometer where changes in laser power, beam alignment, signal to noise ratio, marginal filters, dirty optics or brewster windows, etc. might require recalibration of the instrument. Fluorescent microspheres can also be used for instrument alignment purposes and to check for instrument drift during the analysis of multiple samples. However, microspheres do not permit compensation for staining variations which is possible with P.berghei infected blood cells. Operationally, when the malaria infected blood is fixed and stained as described in the present invention, the red and green fluorescent peaks can routinely be set at specific channels (e.g., channel 23 for single parasitezed cells and channel 257 fpr CD71 positive cells, respectively. The malarial parasite infected blood is used as a biological standard for setting up acquisition and analysis dot plots essentially as described in Tometsko (1993, U.S. Pat. No. 5,229,265), which method is incorporated herein by reference. Briefly, a dot plot is created that has FSC (forward angle light scatter) as the X parameter (either in log scale or linear scale) and SSC (side angle light scatter) as the Y parameter as shown in FIGS. 1$a$ and 1$b$. A gate is set around total peripheral blood cells. A second plot (FIG. 2) is then generated for FL2 (red fluorescence generated from the propidium iodide) as the X parameter and FL1 (green fluorescence generated from the antibody). Normally with a severe malaria infection there is no green fluorescence associated with the malaria blood samples because anemia results and no new reticulocytes are being produced by the animal. As shown in FIG. 2, the malaria infected blood samples ideal for reliable and repeatable instrument setup are obtained from animals that have either rebounded from the infection or were not as severely treated, in this way, reticulocytes are still present.

PMT voltages and fluorescence compensation are adjusted until the biological standards are positioned at selected locations (e.g., channel 23 for single parasitized cells and channel 257 for CD71 positive cells) to generate a plot similar to FIG. 2. It is important that adjustments are made until the parasites in the RET and NCE populations are in a vertical plane as shown in FIG. 2.

Figure 3A:
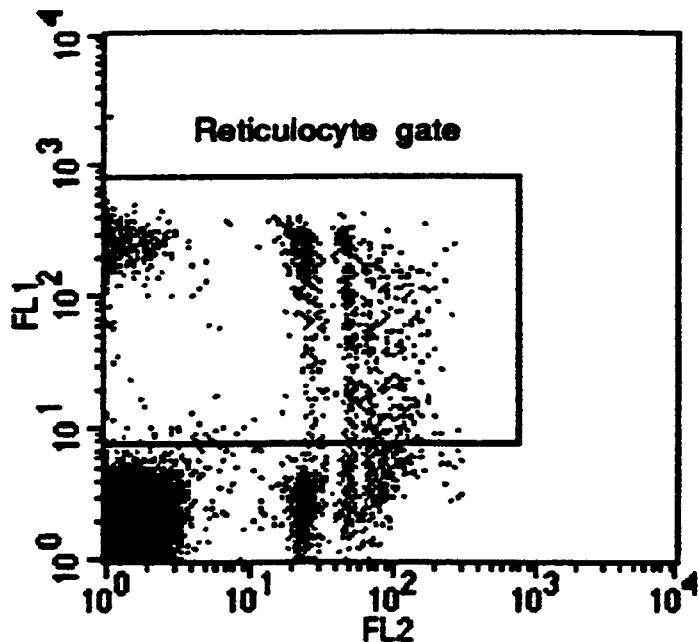
FIG. 3*a* and 3*b* are bivariate plots of green fluorescence (FL1) versus red fluorescence (FL2) for P. berghei infected blood showing the reticulocyte gate (FIG. 3*a*) and the micronucleus gate (FIG. 3*b*).
Figure 3B:
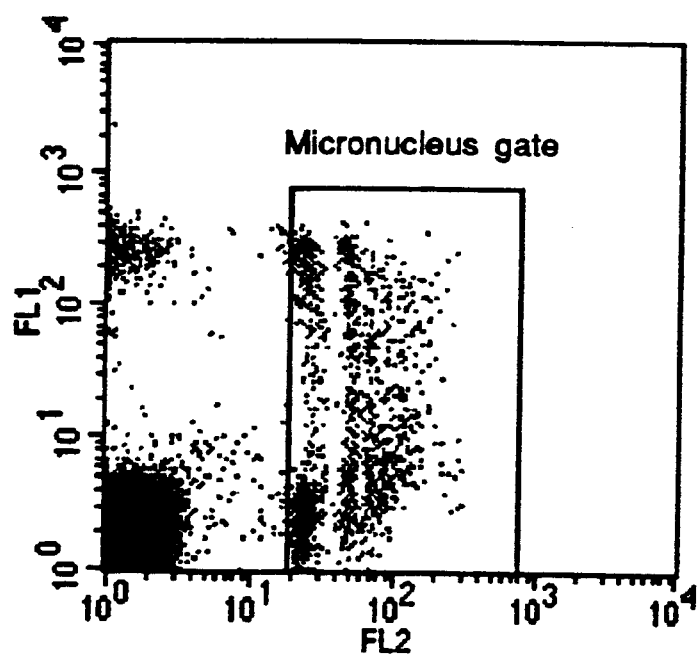

In order to isolate the populations of interest, software gates are placed as shown in FIG. 3$a$. Thee upper part of the unstained NCE population is used as the lower limit for the reticulocyte population and the upper part of the CD71 positive RET population is used as the upper limit. This plot is also used to define the MN population as shown in FIG. 3$b$. The lower edge of the single parasitized population is used as the lower limit for the micronucleus population and the upper limit extends to approximately 2 logs above it.

Superimposition of the two gates is used to generate a bivariate plot to define four populations. The location of the nucleated cells is to the far right in red fluorescence (FIG. 2). This population is also monitored relative to the location of the parasitized cells. PMT voltages, compensation and other factors described herein can be adjusted to set the populations to specific points.

As an illustration, Erythrocytes were isolated by gating on forward and side light scatter parameters. The stop mode of each analysis was reached when 500,000 total erythrocytes were interrogated. A typical blood sample bivariate plot (FIG. 4) is obtained. A window was set up corresponding to cells low in both fluorescence due to the labeled antibody with binding specificity for a surface marker for erythroblasts/reticulocytes (e.g., anti-CD71 antibody) and fluorescence due to the nucleic acid staining dye (e.g., propidium iodide), such as for detecting normochromatic erythrocytes in the erythrocyte population. A second gate was used to define cells low in anti-CD71 fluorescence and high in propidium iodide fluorescence, such as for detecting micro-nucleated normochromatic erythrocytes in the erythrocyte population. A third region was defined corresponding to cells which were high in anti-CD71 fluorescence and low in propidium iodide fluorescence, such as for detecting reticulocytes in the erythrocyte population. A fourth region corresponding to cells which were high in both anti-CD71 fluorescence and in propidium iodide fluorescence was defined for detecting micronucleated reticulocytes in the erythrocyte population. Having defined these regions using the malaria infected blood, the frequency of reticulocytes, micronucleated reticulocytes, micronucleated normochromatic erythrocytes, and normochromatic erythrocytes were automatically determined by the flow cytometry software.

EXAMPLE 3
Staining Of The Surface Marker For Erythroblasts/Reticulocytes By Antibody It is known to practitioners in the art that reticulocytes express certain surface markers which can be used to distinguish reticulocytes from mature erythrocytes. One such marker is the CD71-defined antigen, the transferrin receptor. Fluorescent anti-transferrin receptor antibodies have been used to differentially stain and score reticulocytes via flow cytometry technology (Seligman et al., 1983, *Am. J. Hematology* 14:57–66; Serke et al., 1992, *British J. Haematology* 81:432–439). Various protocols are known in the art for labeling antibody with a fluorescent label. For example, a general protocol for labeling the antibody with FITC is as follows. The antibody, in a concentration of from 0.1 to 10 mg/ml, is dissolved in 0.1 to 0.2 M bicarbonate buffer (pH 8.3 to 9). The antibody is then incubated with FITC (1 mg/ml) with continuous stirring for 1 hour at 22° C. in a labeling buffer of 0.1 M sodium bicarbonate (pH 9.0). The reaction is stopped with hydroxylamine (0.15 M final concentration, freshly prepared), incubated for 1 hour, after which the labeled antibody is dialyzed extensively in the dark at 4° C., and then stored at −75° C. until used. Alternatively, to remove unincorporated fluorescent label from the labeled antibody, the antibody can be subjected to molecular sieve chromatography.

In further illustrating this embodiment, experiments were performed to optimize the resolution of the fluorescein isothiocyanate conjugated anti-CD71 antibody (purchased commercially) labeled reticulocytes. For this experiment, 20 $\mu$l of fixed cells were added to 80 $\mu$l of working FITC-anti-CD71 antibody solutions covering a range of concentrations (0–30 $\mu$l stock FITC-anti-CD71 antibody/ml bicarbonate buffer). After 30 minutes at 4° C., 1 ml bicarbonate buffer was added and the cells were analyzed via flow cytometry to evaluate effective FITC-anti-CD71 antibody concentrations. The PMT voltage settings of the flow cytometer were adjusted to provide maximum resolution of the reticulocyte population. The results, shown in Table 1, suggest that with these conditions, the concentration of FITC-anti-CD71 antibody in the working solution may be between 5 $\mu$l and 30 $\mu$l stock FITC-anti-CD71 antibody/ml bicarbonate buffer.

TABLE 1

| Volume of Stock ($\mu$l/ml) FITC-anti-CD71 Ab | % FITC-anti-CD71 Ab Positive Cells |
| --- | --- |
| 0 | 0.01 |
| 5 | 1.62 |
| 10 | 1.61 |
| 20 | 1.66 |
| 30 | 1.79 |

In a preferred method, 20 $\mu$l of the fixed cell suspension is added to 80 $\mu$l working FITC-anti-CD71 antibody solution (10 $\mu$l stock FITC-anti-CD71 antibody/ml bicarbonate buffer (and incubated at 4° C. After 30 minutes, 1 ml of bicarbonate buffer is added and the cells are ready for flow cytometric analysis. By performing the labeling procedure in a low volume, the need to centrifuge and wash cells is eliminated.

Subsequent to determining an appropriate immunofluorescent labeling procedure for resolving mammalian peripheral blood reticulocytes, an experiment was performed to demonstrate the relevance the CD71 positive phenotype to micronucleus analyses. In this experiment, one mammal was treated in a manner which is know to stimulate erythropoiesis, and another mammal was exposed to a drug which inhibits hematopoietic function. Specifically, one female mouse (BALB/c) was bled extensively at time 0 hours (approximately 300 $\mu$l) in order to induce red blood cell production. Subsequent blood samples were collected at 24 and 48 hours to track the influx of immature erythrocytes into the peripheral blood pool. A second female mouse was also bled at 0, 24 and 48 hours, although not as extensively. To impair erythropoiesis, this animal was treated with methotrexate (50 mg methotrexate/kg body weight) via intraperitoneal injection at time 0 and at 24 hours.

Each of the 6 blood samples collected from the 2 animals was fixed and analyzed for reticulocyte content via flow cytometry. These measurements were determined using two methods. The first method employed the nucleic acid staining dye propidium iodide. Similar to new methylene blue or acridine orange, propidium iodide differentially stains the immature erythrocytes based on their RNA content (Wallen et al., 1980, *Cytometry* 3:155). For this analysis, 20 $\mu$l of fixed blood cells were transferred to tubes containing 1.25 $\mu$g propidium iodide/ml bicarbonate buffer. The samples were analyzed with a flow cytometer providing 488 nm excitation. For each measurement, 500,000 total erythrocytes were interrogated, and the population of cells expressing a high red fluorescent signal (e.g., above channel 150) were scored as RNA-positive reticulocytes. The second method utilized the immunofluorescent reagent, FITC-anti-CD71 antibody. For this analysis, one preferred method involves adding 20 $\mu$l aliquots of fixed blood cells to tubes containing 80 $\mu$ working FITC-anti-CD71 antibody solution (10 $\mu$l stock FITC-anti-CD71 antibody per ml bicarbonate buffer). The cells were placed at 4° C. for 30 minutes, resuspended with 1 ml cold bicarbonate buffer, and analyzed with 488 nm excitation. As with the propidium iodide analyses, 500,000 erythrocytes were interrogated per blood sample. The population of erythrocytes expressing a high green fluorescent signal (e.g., greater than channel 150) were scored as reticulocytes.

Figure 5:
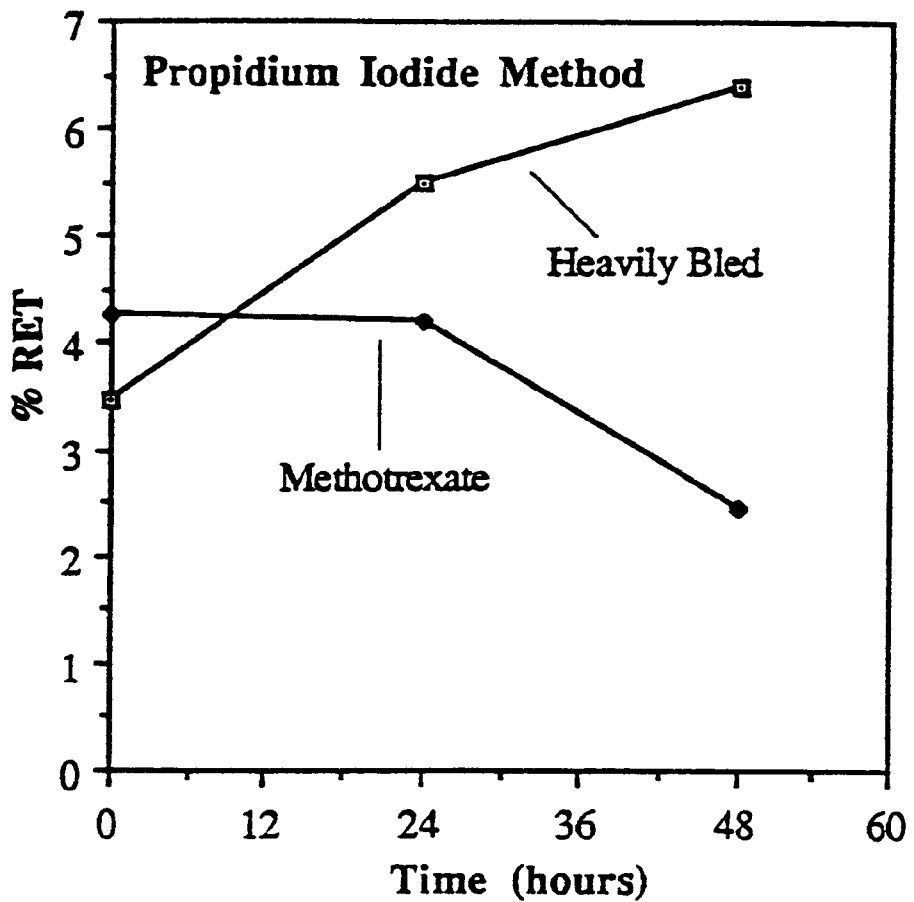
FIG. 5 is a graph showing, as a function of time, the effect of heavy bleeding and methotrexate administration on the percentage of peripheral blood reticulocytes as measured by propidium iodide staining.
Figure 6:
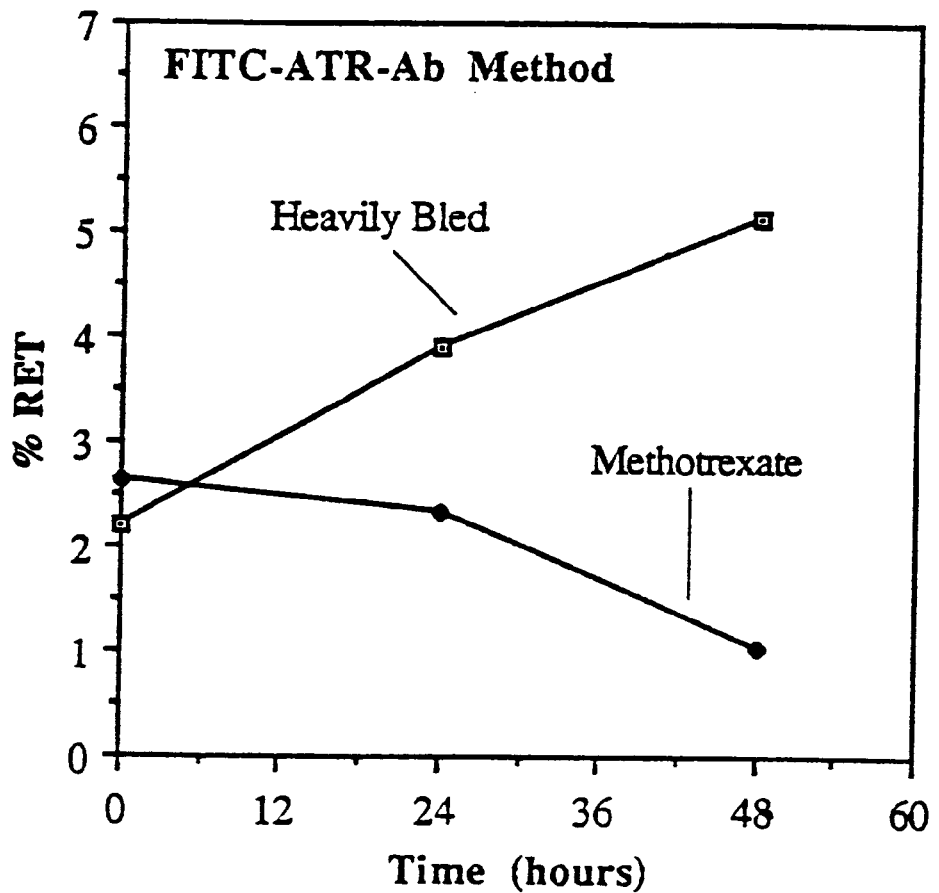
FIG. 6 is a graph showing, as a function of time, the effect of heavy bleeding and methotrexate administration on the percentage of peripheral blood reticulocytes as measured by immunofluorescent technique.

FIGS. 5 and 6 illustrate the effect of bleeding and methotrexate administration on the peripheral blood reticulocyte population as measured by either propidium iodide or FITC-anti-CD71 antibody labeling. As expected, the number of reticulocytes in the heavily bled animal was observed to rise in response to stimulated erythropoietic function. The administration of high dose methotrexate was observed to diminish red blood cell production. In both the erythropoiesis stimulated and inhibited animals, the measurements with the immunofluorescent labeling procedure are found to closely parallel the measurements obtained with the nucleic acid staining method of propidium iodide. Note that the absolute count of reticulocytes is slightly lower for the FITC-anti-CD71 antibody procedure. This is in agreement with other reports which suggest that by using CD71 as a marker, detected is approximately the youngest 70% of the reticulocyte population normally scored with RNA-staining dyes (Serke et al., 1992, supra). These data demonstrate that CD71-positive erythrocytes (erythrocytes bearing a surface marker for erythroblasts/reticulocytes) are extremely well-suited as a target population for the peripheral blood micronucleus assay using the method according to the present invention. Given appropriate blood sampling times, micronuclei events in CD71 positive cells can be attributed to a chemical treatment administered during a recent cell cycle.

EXAMPLE 4
Dual Staining Technique

Propidium iodide and FITC have been employed to simultaneously label nucleic acids and cell surface antigens in human B-cell lymphomas (Kruth et al., 1981, *Cancer Res.* 41:4895–4899; Montecucco et al., 1985, *Basic Appl. Histochem.* 29:275–2821). In the method according to the present invention the combined use of a nucleic acid staining dye, such as propidium iodide, and FITC-antibody labeling is utilized to differentially stain micronucleated reticulocytes. For this procedure, fixed cells (erythrocyte populations) are washed out of methanol as described and stored at 4° C. In a preferred embodiment of the method according to the present invention, 20 µl aliquots of fixed cells are added to tubes containing 80 µl working FITC-anti-CD71 antibody solution with 1 mg ribonuclease A/ml bicarbonate buffer (RNAse A). This solution prepares the cells for scoring by simultaneously labeling reticulocytes with FITC-anti-CD71 antibody and eliminating RNA content. Other RNAse A concentrations are acceptable, but it is necessary for all the RNA to be degraded prior to analysis by this flow cytometric method. Other buffers, such as phosphate-buffered saline, are known to those skilled in the art. After 30 minutes at 4° C. for fixed erythrocytes from peripheral blood samples (and approximately several hours or more at 4° C. for fixed cells from bone marrow preparations), 1 ml cold nucleic acid dye staining solution is added (e.g., 1.25 µg propidium iodide/ml bicarbonate buffer). Note that degradation of reticulocytes' RNA has to be achieved so that fluorescence emitted by the nucleic acid staining dye represents a DNA (micronuclei) specific signal. Following the addition of the nucleic acid staining dye solution, cells are kept at 4° C. until analysis.

In the dual staining process for the method according to the present invention, it may be desirable to have in assay kit form components selected from the group consisting of a fixative solution, nucleic acid staining dye solution, RNAse, a fluorescent-labeled monoclonal antibody with binding specificity for a surface marker for erythroblasts/reticulocytes, a standard buffer as a diluent for the aforementioned components, and various combinations thereof.

It is well appreciated by those skilled in the art that electronic compensation which eliminates the longer wavelength emissions of the FITC signal enhances the resolution of nucleic acid staining dyes and cells tagged by fluorescent-labeled antibody. To optimally resolve the micronucleated reticulocyte population, we set FL2–%FL1 and FL1–%FL2 compensation to 99.6% and 1.2% respectively (FL1= fluorescence one height corresponding to green fluorescence; FL2=fluorescence two height corresponding to red fluorescence ) (CellQuest™ software, Becton Dickinson).

When quantitatively analyzing rare events such as the micronucleated reticulocyte population, it is critical that the flow cytometer's sample tubing is clean and free of debris which may interfere with highly accurate scoring. In that regard, it may be desirable to run a particle-free solution consisting of 1% bleach with 50 mM NaOH in $dH_2O$ through the sample line for approximately one minute before each sample.

EXAMPLE 5
Clastogen Exposure

The method according to the present invention can be used to detect genotoxic or cytogenetic action induced in an individual as a result of exposure to one or more dietary, environmental, or therapeutic factors. After exposure to the factor, a sample of peripheral blood and/or bone marrow is obtained from the individual and assayed for micronuclei events according to the method of the present invention. As an illustration of this embodiment, an experimental model was used to demonstrate the reliability with which dual staining according to the method of the present invention can enumerate micro-nucleated erythrocyte populations. Either peripheral blood or bone marrow cell preparations may be analyzed for the presence of micronucleated erythrocyte populations in this model. For this illustration, five male BALB/c mice were treated with 100 mg methyl methanesulfonate/kg body weight via intraperitoneal injection at time 0 hour. Methyl methanesulfonate (MMS) was chosen as a model clastogen because it has been carefully studied in other mouse micronucleus systems (see, e.g., Tsuyoshi et al., 1989, *Mutation Res.* 223:383–386; Sugiyama et al., 1992, *Mutation Res.* 278:117–120). Consequently, data obtained by the method according to the present invention can be easily compared to data obtained from other scoring methodologies. However, it is appreciated by those skilled in the art that administered to the experimental model may be a known clastogen or a composition suspected of having genotoxic or cytogenetic activity (collectively referred to as a "clastogenic agent"). Alternatively a clastogenic agent may be administered, and within relatively the same time period (from 0 hour to several hours before or after) a composition suspected of having a protective effect (anticlastogen) against the activity of such clastogenic agent may also be administered. The assay is then performed to determine the protective effect of the anticlastogen. For example, chlorophyllin is an in vivo anticlastogen which, when administered 2 hours before clastogen exposure, reduced the incidence of micronucleated polychromatic erythrocytes induced by gamma radiation in mice (Abraham et al., 1994, *Mutat. Res.* 322:209–212).

To closely evaluate the effectiveness and reliability of this automated scoring method, an experiment was designed to track the incidence of micronuclei in the peripheral blood of mice after an acute (single) exposure to clastogen. Immediately after obtaining initial (time 0 hour) blood samples from 5 male mice, each animal was injected with 100 mg MMS/kg body weight. Clastogen was delivered in a volume of 25 μl/kg body weight. Subsequent blood samples were collected at 24, 40, 48 and 72 hours. Blood samples were fixed and stored at −70° C. until completion of the experiment.

Fixed cells were washed out of methanol as described and stored at 4° C. In a preferred embodiment of the present invention, 20 μl aliquots of fixed blood cells were added to tubes containing 80 μl working FITC-anti-CD71 antibody solution with 1 mg RNAse A/ml bicarbonate buffer. After 30 minutes at 4° C., 1 ml cold propidium iodide staining solution was added (1.25 μg propidium iodide/ml bicarbonate buffer). Following the addition of the propidium iodide staining solution, cells were kept at 4° C. until analysis. Quantitative analysis was performed using the method according to the present invention and the number of normochromatic erythrocytes, micronucleated normochromatic erythrocytes, reticulocytes, and micronucleated reticulocytes were determined. These data are presented in Table 2.

TABLE 2

Flow cytometric analysis of MMS-induced micronuclei

| Time (hrs) | Mouse No. | No. NCE | No. MN-NCE | Freq. (%) MN-NCE | No. RET | No. MN-RET | Freq. (%) MN-RET |
|---|---|---|---|---|---|---|---|
| 0 | 1 | 490631 | 1339 | 0.27 | 8471 | 26 | 0.31 |
|   | 2 | 490648 | 1240 | 0.25 | 8541 | 23 | 0.27 |
|   | 3 | 489526 | 1111 | 0.23 | 9825 | 24 | 0.25 |
|   | 4 | 491259 | 1150 | 0.23 | 7883 | 21 | 0.27 |
|   | 5 | 493156 | 1390 | 0.28 | 6030 | 16 | 0.27 |
|   | Average |  |  | 0.25 |  |  | 0.27 |
| 24 | 1 | 490949 | 1244 | 0.25 | 8531 | 46 | 0.54 |
|   | 2 | 490112 | 1287 | 0.26 | 9390 | 88 | 0.93 |
|   | 3 | 488089 | 1145 | 0.23 | 11532 | 80 | 0.69 |
|   | 4 | 487462 | 1254 | 0.26 | 12234 | 162 | 1.31 |
|   | 5 | 490011 | 1391 | 0.28 | 9391 | 55 | 0.58 |
|   | Average |  |  | 0.26 |  |  | 0.81 |
| 40 | 1 | 490511 | 1405 | 0.29 | 8373 | 386 | 4.41 |
|   | 2 | 485301 | 1285 | 0.26 | 13570 | 592 | 4.18 |
|   | 3 | 486302 | 1178 | 0.24 | 12679 | 652 | 4.89 |
|   | 4 | 484237 | 1445 | 0.30 | 14533 | 581 | 3.81 |
|   | 5 | 492350 | 1458 | 0.30 | 6785 | 262 | 3.72 |
|   | Average |  |  | 0.28 |  |  | 4.20 |
| 48 | 1 | 487164 | 1515 | 0.31 | 11794 | 355 | 2.92 |
|   | 2 | 481651 | 1538 | 0.32 | 17187 | 366 | 2.09 |
|   | 3 | 480648 | 1298 | 0.27 | 18484 | 396 | 2.10 |
|   | 4 | 476364 | 1517 | 0.32 | 22687 | 431 | 1.86 |
|   | 5 | 490250 | 1339 | 0.27 | 8990 | 211 | 2.29 |
|   | Average |  |  | 0.30 |  |  | 2.25 |
| 72 | 1 | 473052 | 1593 | 0.34 | 25838 | 112 | 0.43 |
|   | 2 | 462539 | 1573 | 0.34 | 36327 | 147 | 0.40 |
|   | 3 | 450096 | 1607 | 0.36 | 48913 | 224 | 0.46 |
|   | 4 | 461882 | 1628 | 0.35 | 36940 | 150 | 0.40 |
|   | 5 | 475141 | 1575 | 0.33 | 23744 | 82 | 0.34 |
|   | Average |  |  | 0.34 |  |  | 0.41 |

Abbreviations:
NCE = normochromatic erythrocytes;
MN-NCE = micronucleated normochromatic erythrocytes;
RET = reticulocytes;
MN-RET = micronucleated reticulocytes The mean micronuclei frequency in the mature normochromatic erythrocyte population was found to rise gradually over the course of the experiment: 0.25% initially and 0.34% by 72 hours. The modest effect on the mature erythrocyte population is expected, since MMS-induced micronuclei are diluted by the vast pool of pre-existing cells. Conversely, the frequency of micronuclei events in the reticulocyte population was observed to rise sharply over the course of the first 40 hours, reaching a maximal level of 4.20% The incidence of micronucleated reticulocytes proceeds to fall to nearly background frequencies by 72 hours (0.41%). The highly temporal effect of acute MMS exposure on micronuclei frequency in the short-lived reticulocyte population is expected. The clastogenic action exerted by MMS reaches a maximum level and then quickly subsides as the hydrophilic compound is metabolized and excreted. The potency and kinetics of MMS-induced micronuclei formation are in good agreement with previous observations using different methodologies (see, Sugiyama et al. 1992, supra). While the previous observations did not include a 40 hour sample, observed was a maximum response between the 24 and 48 hour sampling times (i.e., 36 hours).

Aside from comparing micronuclei frequencies over time, it is informative to study the frequency of micronuclei events in the set of 0 hour samples. As indicated by Table 2, the mean frequency of micronucleated normochromatic erythrocytes and micronucleated reticulocytes are very similar at time 0 hour (0.25% versus 0.27%, respectively). We would expect these values to be approximately equal, since mice do not effectively clear micronuclei from circulation. Note that before optimal staining and flow cytometric operating procedures were realized, these values often diverged significantly. Thus, for the experimental model, a correspondence between these numbers is one useful tool which provides evidence that micronucleated normochromatic erythrocytes and micronucleated reticulocytes populations are being scored reliably and with precision.

Figure 7:
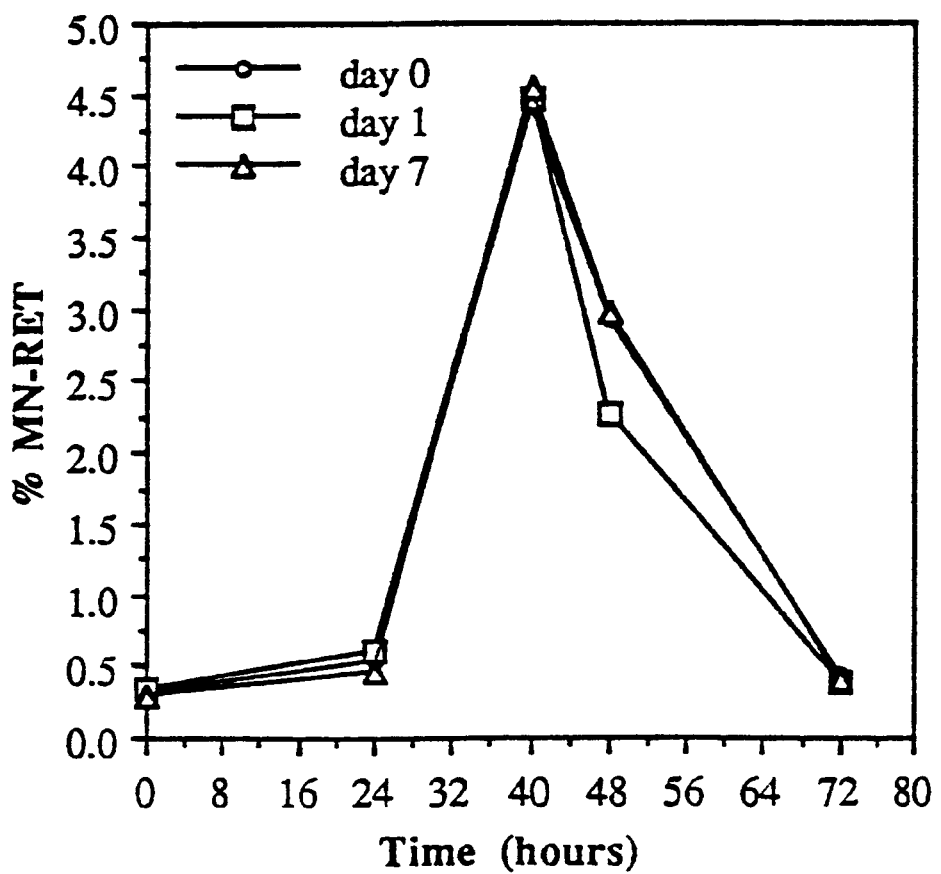
FIG. 7. is a graph illustrating the incidence of micronucleated reticulocytes, as tracked over 72 hours, in the peripheral blood pool of a mouse injected with methyl methanesulfonate.

To evaluate the consistency of measurements obtained by the method according to the present invention, an experiment was performed with blood samples obtained from MMS mouse no. 1. For this evaluation, each of the animal's 5 blood samples were prepared for flow cytometric analysis using the method according to the present invention, and scored one day and again seven days after the initial measurements reported in Table 2. These data are graphically presented in FIG. 7, wherein measurements from day 0 (-o-) are compared to those from day 1 (-□-) and from day 7 (-Δ-). The high reproducibility of the resultant measurements suggest that fixed samples can be stored at 4° C. for at least one week without appreciable loss in scoring reliability, and support the consistency of the flow cytometric scoring when using the method according to the present invention.

The data reported for the MMS experiment suggest that the analysis windows used to define the micronucleated normochromatic erythrocytes and micronucleated reticulocyte populations are highly appropriate. Over the 72 hour experimental time-frame, the incidence of micronuclei in the micronucleated normochromatic erythrocyte population rose slightly, and the frequency of micronucleated reticulocytes was observed to rise and fall quickly. Given the persistence of these populations in the peripheral blood pool of mice, these profiles are expected. Furthermore, the high reproducibility found when blood samples from an MMS-treated mouse were re-analyzed over the course of a week suggests that the analysis windows can be used to compare flow cytometric data obtained on different days.

In another illustration of this embodiment, the incidence of micronuclei was determined in the peripheral blood of rats, wherein like humans, micronucleated erythrocytes are captured by the spleen. Adult male Sprague-Dawley rats were treated with a dose range of a clastogen, cyclophosphamide (CP). Five animals were used for each dose of 0,5,10, and 20 mg CP/kg body weight. All exposures were via oral gavage. Saline (control) and CP were delivered in a volume of 10 ml/kg body weight. Blood samples were obtained for both FCM and microscopic analyses 48 hours post exposure.

Figure 8:
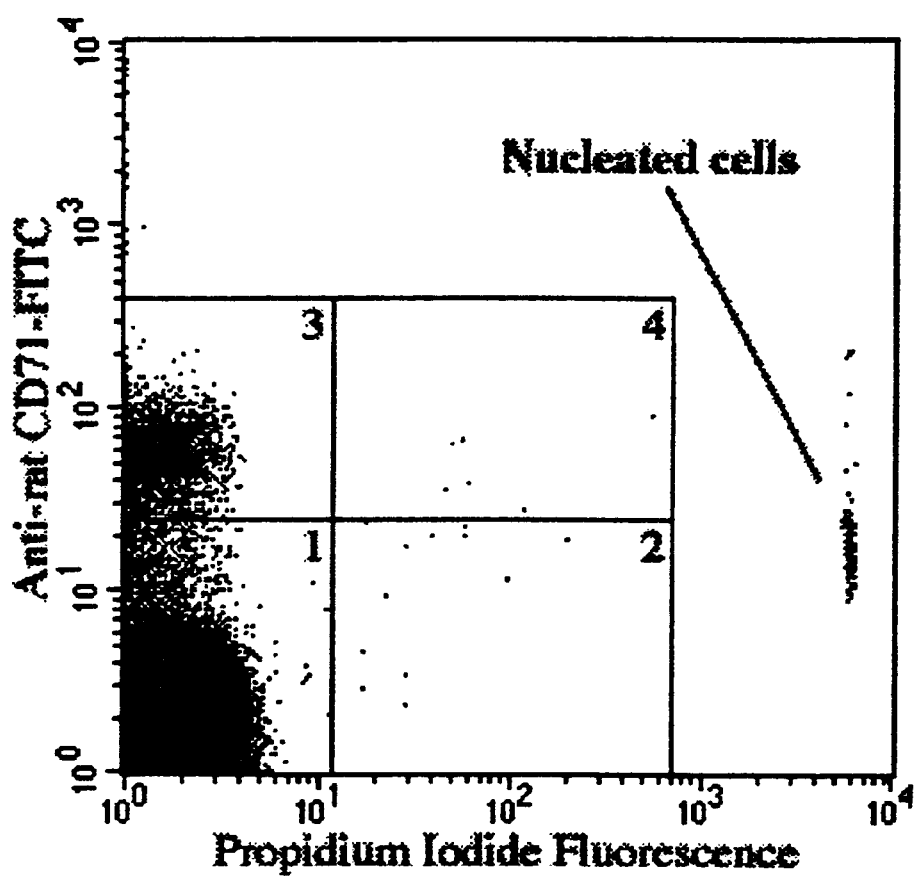
FIG. 8. is a bivariate graph illustrating the resolution of rat erythrocyte populations. Window no. 1 corresponds to cells which are low in green and red fluorescence, i.e. normochromatic erythrocytes. Window no. 2 corresponds to cells high in red fluorescence, i.e., micronucleated normochromatic erythrocytes. Window no. 3 corresponds to cells high in green fluorescence, i.e., reticulocytes. Window no. 4 corresponds to cells high in both red and green fluorescence, i.e., micronucleated reticulocytes.

For flow cytometric analysis, peripheral blood samples were obtained and processed as described above for mice except that the anti-CD71 reagent utilized in this experiment was specific for rat. Blood samples were maintained at room temperature for no more than two hours before being fixed. Cells were fixed with ultracold methanol and washed as described previously. The stop mode for these analyses was the acquisition of 10,000 total RETs. A higher CD71-associated fluorescent threshold is used relative to the one employed for mouse samples (FIG. 8). This allows the analysis of micronucleated reticulocytes to be restricted to the youngest fraction of reticulocytes.

For manual analysis, blood was also collected from each rat at the same time as for FCM analysis. Microscopic inspection according to the method of Hayashi et al. (1990, *Mutation Research*, 245:245–249) which method is hereby incorporated by reference was carried out. The frequencies of micronucleated peripheral blood reticulocytes were recorded based on the analysis of 1000 Type I and Type II RETs The flow cytometric and corresponding microscopic micronucleus data are presented in Table 3.

TABLE 3

| Treatment | Rat No. | Freq. (%) MN-RETs[a] FCM | Freq. (%) MN-RETs[b] Microscopic |
|---|---|---|---|
| Saline | 1 | 0.08 | 0.0 |
|  | 2 | 0.04 | 0.1 |
|  | 3 | 0.02 | 0.1 |
|  | 4 | 0.06 | 0.2 |
|  | 5 | 0.08 | 0.0 |
| Average |  | 0.06 | 0.1 |
| Std. Dev. |  | 0.03 | 0.08 |
| Cyclophosphamide | 6 | 0.16 | 0.3 |
| 5 mg/kg BW | 7 | 0.09 | 0.2 |
|  | 8 | 0.12 | 0.3 |
|  | 9 | 0.12 | 0.2 |
|  | 10 | 0.13 | 0.2 |
| Average |  | 0.12* | 0.2* |
| Std. Dev. |  | 0.03 | 0.05 |
| Cyclophosphamide | 11 | 0.18 | 0.4 |
| 10 mg/kg BW | 12 | 0.22 | 0.1 |
|  | 13 | 0.32 | 0.1 |
|  | 14 | 0.25 | 0.2 |
|  | 15 | 0.19 | 0.6 |
| Average |  | 0.23** | 0.3* |
| Std. Dev. |  | 0.06 | 0.22 |
| Cyclophosphamide | 16 | 0.63 | 0.8 |
| 20 mg/kg BW | 17 | 1.12 | 0.5 |
|  | 18 | 0.62 | 1.3 |
|  | 19 | 0.79 | 1.0 |
|  | 20 | 0.98 | 1.2 |
| Average |  | 0.83** | 1.0* |

[a]MN-RET frequencies were determined by evaluating 10,000 high CD71 RETs per sample via flow cytometry.
[b]MN-RET frequencies were determined by evaluating 1,000 total RETS per sample microscopically with AO-stained slides.
*indicates $p \leq 0.05$ (95% confidence interval) when compared to control group, one tailed t-test.
**indicates $p \leq 0.0001$ (99.9% confidence interval) when compared to control group, one tailed t-test.

One tailed-t tests were used to evaluate the mean frequency of micronucleated reticulocytes in control versus CP-treated animals. These results indicate that the method of the present invention can be used to determine differences in the frequency of micronucleated reticulocytes following clastogen exposure. That is, the MN-RET frequency measurements provide a clear indication of genotoxicity at all dose levels by both flow cytometry and microscopic inspection. Further, the FCM method is more sensitive than the manual determination since data presented in Table 3 indicates that the medium and high dose treatment groups are significantly different from control animals at the 99.9% confidence interval, in comparison to 95% with manual scoring.

EXAMPLE 6

This embodiment illustrates the temperature range during the fixation step of the method of the present invention. As described in Example 1, the fixative should be at temperature of between −40° C. to −90° C. for the process of the present invention. In this embodiment samples were fixed at selected temperatures and MN-RET frequency was used as an indicator of sample quality because of its reliability and sensitivity. Following collection of blood as described in Example 1, the samples were fixed in methanol at −20° C., −40° C. or −75° C., or in isopropyl alcohol at −40° C. At a temperature of −20° C., there was significant aggregation. The results for fixation at −40° C. and −75° C. are presented in Table 4.

TABLE 4

Flow cytometric analysis using various fixation conditions

| Sample | Alcohol | Temperature | Freq. (%) MN-RETs |
|---|---|---|---|
| 1 | Methanol | −75° C. | 0.26 |
| 2 | Methanol | −75° C. | 0.27 |
| 3 | Methanol | −75° C. | 0.29 |
| Average |  |  | 0.27 |
| 1 | Isopropyl | −40° C. | 0.22 |
| 2 | Isopropyl | −40° C. | 0.25 |
| 3 | Isopropyl | −40° C. | 0.25 |
| Average |  |  | 0.24 |
| 1 | Methanol | −40° C. | 0.26 |
| 2 | Methanol | −40° C. | 0.33 |
| 3 | Methanol | −40° C. | 0.30 |
| Average |  |  | 0.30 |

From the foregoing description, one skilled in the art will be capable of analyzing peripheral blood or bone marrow cell preparations for the presence of micronucleated normochromatic erythrocytes and micronucleated reticulocytes by flow cytometry. Obvious modifications and variations, such as substitution of equivalents or adaptation for various applications, will be apparent to one skilled in the art from the foregoing description, and such are considered within the scope of the claimed invention.

What is claimed is:

1. A single laser flow cytometric method for the enumeration of micronuclei events in erythrocyte populations, the method comprising the steps of:

a) obtaining a sample of erythrocyte populations from an individual, wherein the sample is from an origin selected from the group consisting of peripheral blood and bone marrow;

b) fixing the erythrocytes in said sample in an alcohol at a temperature of from about −40° C. to about −90° C. so as to cause the erythrocytes to be in suspension and free of aggregates, be permeable to a nucleic acid dye and RNase, maintain cell surface markers in a form recognizable by antibody, and exhibit low autofluorescence;

(c) simultaneously degrading RNA of reticulocytes in the fixed erythrocytes with RNase, and contacting the reticulocytes with a fluorescent labeled antibody having binding specificity for a surface marker for erythroblasts/reticulocytes;

(d) staining in the erythrocyte populations DNA representing micronuclei with a nucleic acid staining dye in a concentration range detectable by flow cytometry;

(e) exciting the nucleic acid staining dye and the fluorescent label associated with the erythrocyte populations with a focused laser beam of appropriate excitation wavelength for both the nucleic acid staining dye and the fluorescent label to produce fluorescent emission; and (f) detecting the fluorescent emission and light scatter produced by the erythrocyte populations and calculating the number of specific erythrocyte populations in said sample, wherein the specific erythrocyte populations are selected from the group consisting of mature normochromatic erythrocytes, reticulocytes, micronucleated normochromatic erythrocytes, micronucleated reticulocytes, and a combination thereof.

2. The flow cytometric method according to claim 1, wherein the sample is from peripheral blood.

3. The flow cytometric method according to claim 1, wherein the sample is from bone marrow.

4. The flow cytometric method according to claim 1, wherein the alcohol is a primary alcohol at a temperature of about −40° C. to about −70° C.

5. The flow cytometric method according to claim 1, wherein the primary alcohol is ethanol.

6. The flow cytometric method according to claim 4, wherein the primary alcohol is methanol.

7. The flow cytometric method according to claim 1, wherein the alcohol is a secondary alcohol.

8. The flow cytometric method according to claim 7, wherein the secondary alcohol is isopropyl alcohol.

9. The flow cytometric method according to claim 1, wherein the fluorescent labeled antibody having binding specificity for a surface marker for erythroblasts/reticulocytes is FITC-anti-CD71 antibody.

10. The flow cytometric method according to claim 1, wherein the nucleic acid staining dye is selected from the group consisting of propidium iodide, ethidium bromide, mithramycin, acridine orange, pyronine Y, and benzathiazolium-4-quinolinium dimer TOTO-1.

11. The flow cytometric method according to claim 10, wherein the nucleic acid staining dye consists of propidium iodide.

12. The flow cytometric method according to claim 1, further comprising administering a clastogenic agent to the individual prior to obtaining a sample of the erythrocyte populations from said individual.

13. The flow cytometric method according to claim 12, wherein the sample is from peripheral blood.

14. The flow cytometric method according to claim 12, wherein the sample is from bone marrow.

15. The flow cytometric method according to claim 12, wherein the primary alcohol is ethanol.

16. The flow cytometric method according to claim 15, wherein the primary alcohol is methanol.

17. The flow cytometric method according to claim 12, wherein the fluorescent labeled antibody having binding specificity for a surface marker for erythroblasts/reticulocytes is FITC-anti-CD71 antibody.

18. The flow cytometric method according to claim 12, wherein the nucleic acid staining dye is selected from the group consisting of propidium iodide, ethidium bromide, mithramycin, acridine orange, pyronine Y, and benzathiazolium-4-quinolinium dimer TOTO-1.

19. The flow cytometric method according to claim 18, wherein the nucleic acid staining dye consists of propidium iodide.

20. The flow cytometric method according to claim 12, further comprising administering a suspected anticlastogen to the individual within relatively the same time period of administration of clastogenic agent in measuring any protective effect induced by the suspected anticlastogen.

21. The flow cytometric method according to claim 20, wherein the sample is from peripheral blood.

22. The flow cytometric method according to claim 20, wherein the sample is from bone marrow.

23. The flow cytometric method according to claim 20, wherein the primary alcohol is ethanol.

24. The flow cytometric method according to claim 23, wherein the primary alcohol is methanol.

25. The flow cytometric method according to claim 20, wherein the fluorescent labeled antibody having binding specificity for a surface marker for erythroblasts/reticulocytes is FITC-anti-CD71 antibody.

26. The flow cytometric method according to claim 20, wherein the nucleic acid staining dye is selected from the group consisting of propidium iodide, ethidium bromide, mithramycin, acridine orange, pyronine Y, and benzathiazolium-4-quinolinium dimer TOTO-1.

27. The flow cytometric method according to claim 26, wherein the nucleic acid staining dye consists of propidium iodide.

* * * * *